United States Patent
Altarac et al.

(10) Patent No.: US 7,232,441 B2
(45) Date of Patent: Jun. 19, 2007

(54) OCCIPITAL PLATE AND ROD SYSTEM

(75) Inventors: Moti Altarac, Aliso Viejo, CA (US); Philip A. Mellinger, Ladera Ranch, CA (US); Alex Vaccaro, Gladwyne, PA (US)

(73) Assignee: Cross Medicalproducts, Inc., Irvine, CA (US)

( * ) Notice: Subject to any disclaimer, the term of this patent is extended or adjusted under 35 U.S.C. 154(b) by 0 days.

(21) Appl. No.: 10/358,684

(22) Filed: Feb. 5, 2003

(65) Prior Publication Data
US 2003/0153913 A1 Aug. 14, 2003

Related U.S. Application Data

(60) Provisional application No. 60/356,705, filed on Feb. 13, 2002.

(51) Int. Cl.
*A61B 17/58* (2006.01)
(52) U.S. Cl. .......................... 606/61; 606/69
(58) Field of Classification Search .................. 606/61, 606/69, 70, 71
See application file for complete search history.

(56) References Cited

U.S. PATENT DOCUMENTS

| | | | |
|---|---|---|---|
| 4,836,193 A | | 6/1989 | Ransford |
| 5,092,893 A | * | 3/1992 | Smith .......................... 606/61 |
| 5,360,429 A | | 11/1994 | Jeanson et al. |
| 5,366,455 A | * | 11/1994 | Dove et al. .................... 606/61 |

(Continued)

FOREIGN PATENT DOCUMENTS

EP 0 308 156 12/1991

(Continued)

*Primary Examiner*—Eduardo C. Robert
*Assistant Examiner*—James L. Swiger
(74) *Attorney, Agent, or Firm*—Hudak, Shunk & Farine Co. LPA

(57) ABSTRACT

The present invention has a plate and rod assembly for implantation in the cervical region of the spine which includes an occipital plate having an angled anchor bridging area that is attached to the lower posterior curve of the skull. On either side the bridging area is connected to offset legs which join flanged areas having a high friction surface and which include tethered rod anchors having rod-receiving channels. These flanges include undercut slots longer in one direction than the other to capture the side plates integral to the open U-shaped members including the rod-receiving channels. The side plates extend longer in the direction of the longitudinal axis of the rod when it is in the channel so that they can thus be lowered into the slot and rotated by 90 degrees to capture the channels in the flanges. The channels are closed by a capnut which has a bottom annular flange that also helps to lock the rod in place. The angle of the rod-receiving flanges relative to the plate bridging area allows the rods to be positioned close to the cervical vertebrae so that they can also be attached to the cervical vertebrae using vertebral anchors. The capnut is self-aligning and includes a visual alignment cue that helps to inhibit cross threading by indicating the proper side for starting the capnut on the threads of the channel. Three debossed dots show the alignment relative to a similarly placed set of dots on the proper side of the rod-receiving channel.

20 Claims, 3 Drawing Sheets

U.S. PATENT DOCUMENTS

| | | |
|---|---|---|
| 5,403,314 A | 4/1995 | Currier |
| 5,531,745 A * | 7/1996 | Ray ............................ 606/61 |
| 5,545,164 A | 8/1996 | Howland |
| 5,558,674 A | 9/1996 | Heggeness et al. |
| 5,582,612 A * | 12/1996 | Lin ............................. 606/61 |
| 5,653,708 A | 8/1997 | Howland |
| 5,928,233 A * | 7/1999 | Apfelbaum et al. .......... 606/61 |
| 6,478,797 B1 * | 11/2002 | Paul ............................ 606/61 |
| 6,524,315 B1 * | 2/2003 | Selvitelli et al. .............. 606/70 |
| 6,547,790 B2 * | 4/2003 | Harkey et al. ................ 606/61 |
| 6,641,583 B2 * | 11/2003 | Shluzas et al. ............... 606/61 |
| 6,902,565 B2 * | 6/2005 | Berger et al. ................. 606/61 |
| 2002/0042614 A1 * | 4/2002 | Ueyama et al. ............... 606/61 |
| 2002/0049446 A1 * | 4/2002 | Harkey et al. ................ 606/70 |

FOREIGN PATENT DOCUMENTS

| | | |
|---|---|---|
| EP | 0 744 923 B1 | 2/1995 |
| EP | 0 737 449 B1 | 3/1996 |
| EP | 1 180 347 A2 | 8/2001 |

* cited by examiner

OCCIPITAL PLATE AND ROD SYSTEM

This patent application is based upon U.S. Provisional Application Ser. No 60/356,705; filed Feb. 13, 2002

The invention relates generally to a spinal implant, and more specifically to a spinal implant for use in the occipito-cervical region of the spine, including an occipital plate for attachment to the lower skull. This plate includes rod attachment flanges having tethered rod-receiving channels. The channels are formed as open grooves in U-shaped rod anchor members which include flat flanges or plates that extend in a plane parallel to the longitudinal axis of the rod. The flanges are captured by the recess area surrounding the bottom of a slot through which the U-shaped rod anchor member projects. The channels are closed so as to capture the rod in position by a cap which tightens onto threads on the U-shaped members. The cap has a visual indicator to facilitate proper alignment and to inhibit cross-threading of the cap on the U-shaped member.

BACKGROUND OF THE INVENTION

Constructs have been designed for some time for implantation in the spine which generally include a series of bone fasteners, such as hooks or screws, that are secured to the vertebrae, and which are used to hold stabilizer means such as a rod or plate that spans several vertebrae for stabilization, fixation, and/or for alignment of the vertebrae.

Typically, a spinal rod assembly includes two sets of rods that are fixed to adjacent vertebrae on either side of the spinous process to span a section of spine. The bone anchors may include a number of fixation means, such as screws or hooks, that are used for fixation to the spine, and anchor means, such as rod anchors that includes means to secure the rod to the fixation means. In some systems these component parts are a single integral unit, while other systems utilize a number of assembled components such as for the anchor portion of the assembly.

There are a number of considerations which go into the design of the assembly. The constructs need to be relatively easy to assemble, to be safe for the area of implantation, to provide for flexibility of use to accommodate a number of different indications for implantation and for variations in individuals who require their use, to be strong, yet minimally invasive and low profile, to be useful for manipulation, as well as for the maintenance of the desired alignment of the spine.

There are spinal systems which have successfully worked out these design criteria for the lumbar and the thoracic areas of the spine. However, the occipito-cervical area is deserving of even closer scrutiny as the areas for implantation become smaller and the associated nerves and arteries need to be identified and avoided. Moreover, there is less muscle mass to cover the implant.

SUMMARY OF THE INVENTION

The present invention provides a plate and rod assembly for implantation in the cervical region of the spine including a plate for attachment to the occipital region of the skull.

The plate has an angled bridging area that is attached to the lower posterior curve of the skull known as the occipital region. On either side the bridging area is connected to offset legs which join flanged areas, i.e. flanges, which include tethered rod-receiving channels which are formed in the rod anchor means or members. These flanges include undercut slots that capture side plates integral to (i.e. unitary with) the open U-shaped anchor members that include the horizontally extending rod-receiving channels which are open to the top to permit top loading of the rod into the channel. The anchor members are cylindrical on the outer surface and in the internal recess to form a hollow tube shape with a closed bottom side. The tube is cut on opposing sides to the depth of the bottom surface to form the U-shape in cross-section. The flanged areas of the occipital plate have a machined (i.e. roughened) high friction top (meaning the surface opposed to the one facing the bone) surface, which is preferably knurled, to bite into the surface of the rod that is received in the channels. The side plates extend longer than the slot dimension in the direction of the longitudinal axis of the rod when it is in the channel. However, the side plates are not as long as the slot dimension in the transverse direction. Thus, the side plates of a U-shaped anchor member can be lowered into the slot and rotated by 90 degrees to capture the side plates of the U-shaped members in the recess surrounding the slot in the flanges of the occipital plate. Preferably, the slots include two parallel undercut recess areas on the bottom side which accommodate the opposing side plates of the U-shaped members. Thus, the U-shaped members are tethered in the occipital plate, and can continue to slide in the respective slot of the flanges in order to allow some variability in the location of the channels. However, the bottom surface of the bottom member of the anchor member includes a projection which limits the rotational movement of the anchor within the slot. This limited freedom facilitates assembly during surgery.

The channels in the U-shaped anchor members are closed from the top by a capnut which has a bottom annular flange that also helps to lock the rod in place. The location of the rod-receiving flanges relative to the plate bridging area allows the rods to be positioned close to the cervical vertebrae so that they can be readily attached to the cervical vertebrae using traditional vertebral anchors. This location also places the highest profile elements of the occipital plate assembly in the area where there is the greatest amount of soft tissue coverage. These anchors typically can be integral anchors that have a U-shaped rod receiving channels portion integral with the bone screw, or the anchors can be more complex assemblies that have a screw that moves relative to the anchor portion which begins as a separate piece assembled to the screw. The bridging area of the plate is located upward, relative to the patient's head, of the flanges in order to allow the anchoring screws to be placed in the occipital plate where the bone is stronger and thicker.

In accordance with another aspect of the invention, the capnut is self-aligning as it includes an internal projection that cooperates with the internal recess of the rod-receiving channel members in the direction of the longitudinal axis of the attachment screw. Further, the capnut includes a visual alignment cue that helps to inhibit cross threading by indicating the proper side for starting the capnut on the threads of the channel. Three debossed dots show the alignment relative to a similarly placed set of dots on the proper side of the rod-receiving channel. The capnut can be used with other rod anchors including but not limited to those previously described as more traditional rod anchors.

OBJECTS OF THE INVENTION

It is an object of the invention to provide an improved means for fixation of a cervical rod to the skull by providing an occipital plate that properly positions the rod-receiving channels, and by providing rod anchor members including the rod-receiving channels that can be moved to accommodate the rod alignment and which can subsequently easily be closed to fix the rod relative to the plate. Additionally a clever method of constructing such an assembly is provided wherein the rod anchor member has side plates, and the rod anchor is lowered into a slot in the occipital plate and turned so that the side plates are captured in the undercut recess in the bottom of the plate along the sides of the slot.

It is a further object of the invention to provide a nut for a U-shaped rod anchor that has means to inhibit cross-threading. This means is a visual indication on both the nut and on the appropriate side of the rod anchor to line the threads for proper threading.

DETAILED DESCRIPTION OF THE DRAWINGS

Figure 1:
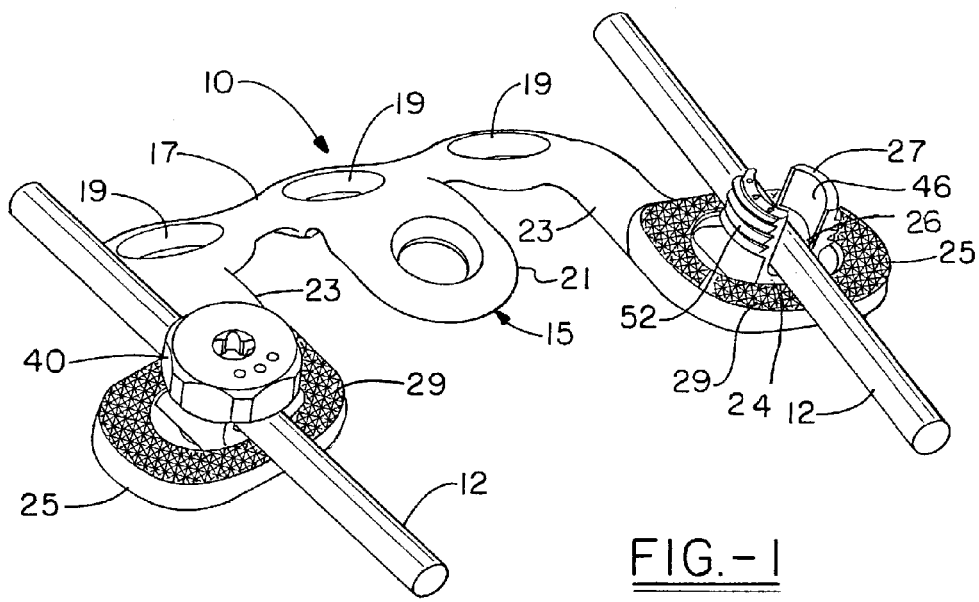
FIG. 1 is a top perspective view of the plate in accordance with the invention showing one rod locked in a rod-receiving channel and a second rod which is not yet locked in position.
Figure 2:
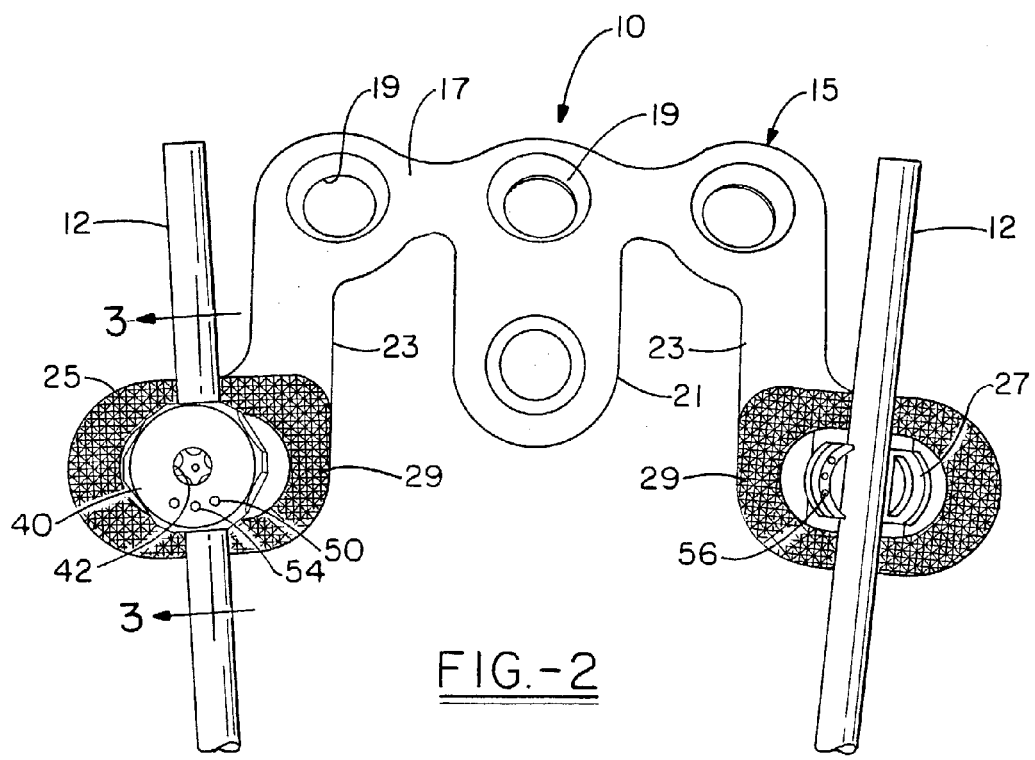
FIG. 2 is a top view of the plate and rod assembly of FIG. 1.
Figure 2A:
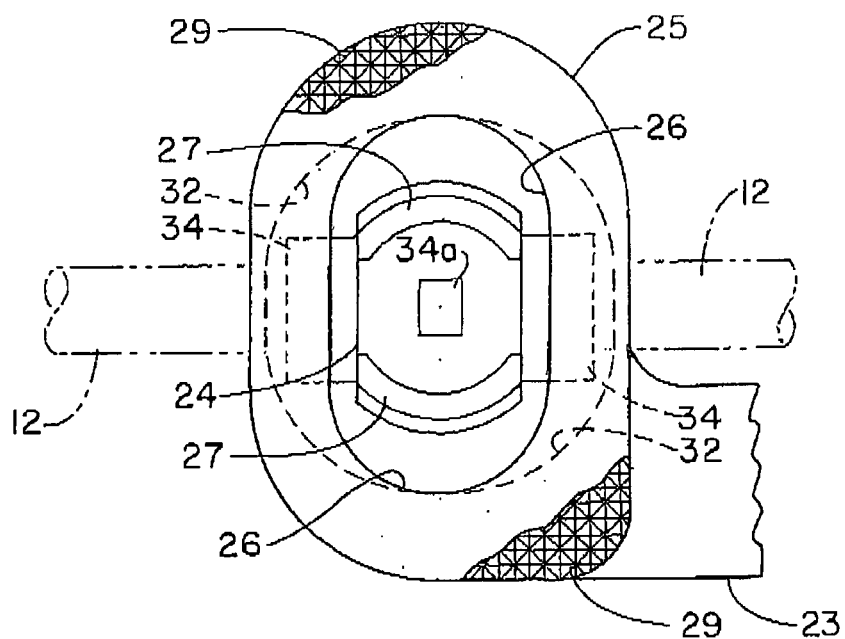
Figure 3:
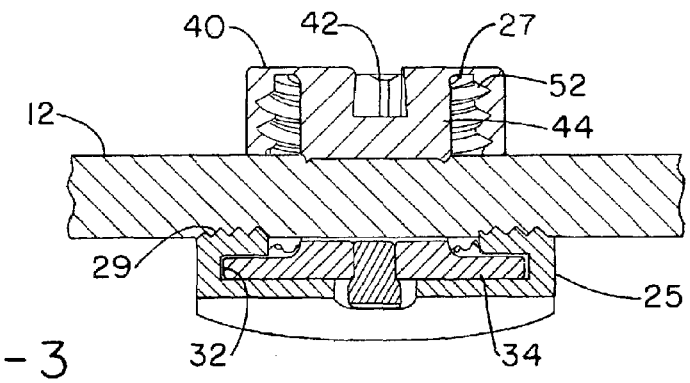
FIG. 3 is a cross-sectional view taken along line 3—3 of FIG. 1.

The present invention involves a spinal implant assembly 10 for use in the occipito-cervical spine which includes a pair of spinal rods 12. The rods 12 are attached to the occipital region of the spine by means of an occipital plate 15. The plate has an upper bridge area 17 that is angled for attachment to the lower posterior curve of the skull known as the occipital region. This bridge area 17 includes countersunk screw holes 19 so that the plate can be fixed to the skull. In addition there is a further central projection 21 which has a hole for fixation. On either side the bridge area 17 is connected to offset legs 23 which join flanged areas 25 that include tethered U-shaped rod anchor members 24 each having an open rod-receiving channel 27. The flanges 25 each have a slot 26 which has a width (i.e. extending along the longer dimension of the flange) that is longer than the height (in the same plane in the direction of the shorter dimension of the flange and parallel to the axis of the rod when it is in the channel.) The flanged areas 25 have a machined (i.e. roughened) high friction top surface 29, which is preferably knurled, to bite into the surface of the rod 12 that is received in the channels 27.

Figure 4:
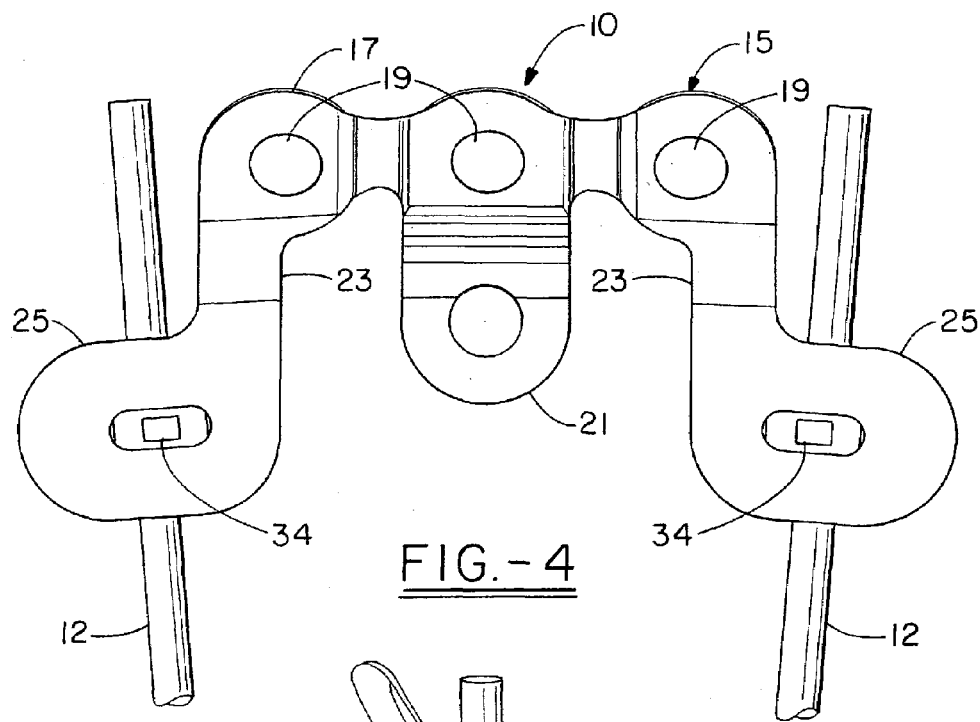
FIG. 4 is a bottom view of the plate and rod assembly of FIG. 1.
Figure 5:
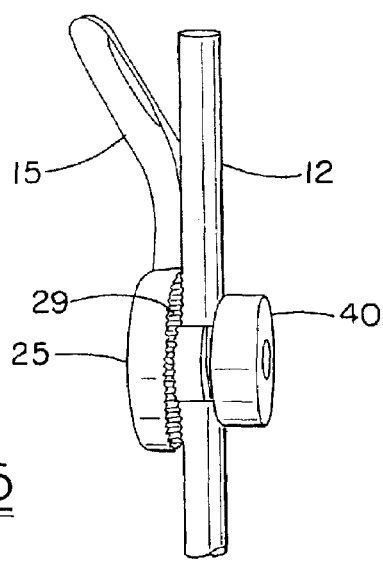
FIG. 5 is a side view of the plate and rod assembly of FIG. 1.

The bottom side of the flanges 25 include an opposing pair of undercut recesses 32 along the long sides of the slots 26 that capture the side plates 34 integral (i.e. unitary) to the U-shaped rod anchor members 24. These members 24 include a central hollow cylindrical portion which has opposing cuts on either side to define an open channel that preferably extends down to the top surface of the flange. The central portion includes threads 52 that could be internal, but are preferably external to permit downward compression by a closure means, such as a cap 40 and/or a nut. The side plates 32 form extension members whichextend outwardly in a direction substantially transverse to the axis of the central portion and in the direction of the axis of the rod-receiving channel. The aggregate length of the side plates from one end to the other is longer than the width of the slot in the same direction (when the rod-receiving channel is in its final alignment). Thus, the side plates are captured in the undercut areas of the slot along the long edges of the slot. However, when the u-shaped member is rotated 90 degrees, the side plates have a length that is shorter than that dimension of the slot, i.e. the long dimension. These side plates can thus be lowered in alignment with the long direction of the slot until it extends below the slot bottom surface and rotated by 90 degrees to capture the channels in the undercut portion of the slots. As is shown in FIG. 4, the slot is open to the bottom, and the U-shaped member includes a rectangular boss 34a on the bottom that maintains some orientation of the u-shaped member in the slot 26. Thus, the U-shaped members are tethered, in the plates 34, but can continue to slide in the flanges in order to allow some play in the location of the channels to facilitate assembly during surgery. The plate is otherwise contoured to minimize the material and the profile.

The channels 27 are closed by a capnut 40 having an internal torque driving recess 42 which has a bottom annular flange or ring that also helps to lock the rod in place. The cross-sectional shape of the ring is preferably v-shaped in order to bite into the rod. The location of the rod-receiving flanges of the plate relative to the plate bridging area allows the rods to be positioned close to the cervical vertebrae so that they can be readily attached to the cervical vertebrae using vertebral anchors. The capnut is self-aligning as it includes an internal projection 44 that cooperates with the internal recess 46 of the rod-receiving channel members in the direction of the longitudinal axis of the attachment screw. Further, the capnut includes a visual alignment indicia 50 that helps to inhibit cross threading by indicating the proper side for starting the capnut on the threads 52 of the channel 27. Both the top surface of the cap, and the top surface of the corresponding side of the U-shaped member have one or more indicia to indicate the proper alignment of the threads relative to each other. Specifically, three debossed dots 54 show the alignment relative to a similarly placed set of dots 56 on the proper side of the rod-receiving channel.

The components of the invention are made from suitable material which is implantable, such as stainless steel or titanium, or ceramic, or composite material.

While in accordance with the patent statutes the best mode and preferred embodiment have been set forth, the scope of the invention is not limited thereto, but rather by the scope of the attached claims.

What is claimed is:

1. A spinal rod assembly comprising a rod and an attachment plate having at least one rod anchor which is a U-shaped member having two upright legs that define a rod-receiving channel, the rod-receiving channel having an outwardly extending side plate, the attachment plate having a bridge area defining a plane and the attachment plate further including a first flange and a second flange, the first flange being attached to a first leg which is offset from the bridge area and the first flange being offset from the first leg; and a second flange being attached to a second leg which is offset from the bridge area and the second flange being offset from the second leg, each flange including one of the rod anchors and each flange defining a flange plane and neither flange plane being co-planar with the plane of the bridge member and each of the first and the second flange includes a recess which retains the side plate of the rod-receiving channel and the flange having a high friction surface which directly contacts the rod when the rod is in the rod-receiving channel.

2. A spinal implant assembly as set forth in claim 1 wherein the high friction surface includes points.

3. A spinal implant assembly as set forth in claim 2 wherein the high friction surface is knurled.

4. A spinal implant assembly as set forth in claim 1 wherein the bridge area defines a plane and has screw holes and the flanges independently define their own planes neither of which are in the same plane as the bridge area.

5. A spinal rod assembly including a rod, a rod anchor and a plate for attachment to an occipital portion of a skull wherein the rod anchor has a U-shaped anchor member with a central vertical axis and which defines a rod-receiving channel for the rod and has an extension member extending in a direction transverse to the central vertical axis and in the direction of the rod-receiving channel to define an extension member length and the anchor member having an anchor member width in the direction transverse to the direction of the extension member, the plate having an upper surface and an opposing lower surface and including a slot extending between the upper and the lower surfaces which surrounds the anchor member, the slot defining a slot width and a slot length, the extension member length being longer than the slot width and the anchor member width being shorter than the slot width so that the anchor member can be inserted into the slot from a direction extending from the upper surface to the lower surface and rotated to capture the anchor member in the slot by means of the extension member when the rod-receiving channel is in its final alignment.

6. A spinal rod assembly as set forth in claim 5 wherein the extension member comprises a side plate.

7. A spinal rod assembly as set forth in claim 6 wherein the anchor member includes two opposing side plates.

8. A spinal rod assembly as set forth in claim 7 wherein the anchor member includes threads and a compression member that holds the rod in place in the rod-receiving channel.

9. A spinal rod assembly as set forth in claim 8 wherein the slot includes two recesses which are defined by undercut areas along the sides of the slot.

10. A spinal rod assembly as set forth in claim 7 wherein the threads are external threads and the compression member is a cap or a nut or a capnut.

11. A spinal rod assembly as set forth in claim 10 wherein the rod anchor has a bottom surface which includes a boss that helps to limit the movement of the rod anchor relative to the slot.

12. A spinal rod assembly as set forth in claim 11 wherein the assembly includes screws, and the plate has a flange which includes the slot and a bridging area with through bores which receive the screws to enable the assembly to be capable of being attached to the skull, and wherein the bridging area is shaped to be placed cranially on the skull relative to the flange.

13. A spinal rod assembly comprising a rod, a rod anchor and an attachment plate having at least two rod anchors each of which comprises a U-shaped member having two upright legs that define a rod-receiving channel, the attachment plate including a bridge area having screw holes and defining a plane and the attachment plate further including a first flange and a second flange, the first flange being attached to a first leg which is offset from the bridge area and the first flange being offset from the first leg; and a second flange being attached to a second leg which is offset from the bridge area and the second flange being offset from the second leg, each flange including one of the rod anchors and each flange defining a flange plane and neither flange plane being co-planar with the plane of the bridge member.

14. A spinal rod assembly as set forth in claim 13 wherein U-shaped member having two upright legs and the anchor further has an outwardly extending side plate, the attachment plate including a recess that retains the side plate.

15. A spinal rod assembly as set forth in claim 14 wherein the recess is formed in a flange of the attachment plate that has an upper surface that is a high friction surface.

16. A spinal implant assembly as set forth in claim 15 wherein the high friction surface includes points.

17. A spinal implant assembly as set forth in claim 13 wherein the two upright legs are threaded and the assembly further includes a threaded locking member that cooperates with the threads on the upright legs to hold the rod in the channel, and wherein the locking member is a capnut and the channel and the capnut each have a top surface with a visual indicator for the proper starting alignment of the locking member.

18. A spinal implant as set forth in claim 17 wherein the channel includes external threads and the locking member includes internal threads.

19. A spinal implant assembly as set forth in claim 18 wherein the visual indication comprises a debossed dot.

20. A spinal implant assembly as set forth in claim 19 wherein the visual indication comprises a series of dots.

* * * * *